United States Patent
Braig et al.

(10) Patent No.: US 6,678,542 B2
(45) Date of Patent: Jan. 13, 2004

(54) CALIBRATOR CONFIGURED FOR USE WITH NONINVASIVE ANALYTE-CONCENTRATION MONITOR AND EMPLOYING TRADITIONAL MEASUREMENTS

(75) Inventors: James R. Braig, Piedmont, CA (US); Peter Rule, Los Altos Hills, CA (US); Bernhard B. Sterling, Danville, CA (US); Heidi M. Smith, Union City, CA (US); Julian M. Cortella, Alameda, CA (US); Jennifer H. Gable, Walnut Creek, CA (US)

(73) Assignee: OptiScan Biomedical Corp., Alameda, CA (US)

( * ) Notice: Subject to any disclaimer, the term of this patent is extended or adjusted under 35 U.S.C. 154(b) by 0 days.

(21) Appl. No.: 10/015,932

(22) Filed: Nov. 2, 2001

(65) Prior Publication Data

US 2003/0036688 A1 Feb. 20, 2003

Related U.S. Application Data

(60) Provisional application No. 60/313,082, filed on Aug. 16, 2001.

(51) Int. Cl.$^7$ ................................................. A61B 5/00
(52) U.S. Cl. ........................ 600/316; 600/310; 600/365
(58) Field of Search ................................. 600/310, 316, 600/322, 331, 326, 365, 309

(56) References Cited

U.S. PATENT DOCUMENTS

| | | | |
|---|---|---|---|
| 5,068,536 A | * 11/1991 | Rosenthal | 600/316 |
| 5,107,469 A | * 4/1992 | Dodson | 368/109 |
| 5,362,966 A | * 11/1994 | Rosenthal et al. | 600/310 |
| 5,507,288 A | * 4/1996 | Bocker et al. | 600/322 |
| 5,753,452 A | * 5/1998 | Smith | 435/14 |
| 5,769,076 A | 6/1998 | Maekawa et al. | |
| 5,991,648 A | 11/1999 | Levin | |
| 6,023,629 A | 2/2000 | Tamada | |
| 6,025,597 A | * 2/2000 | Sterling et al. | 250/341.6 |
| 6,063,039 A | * 5/2000 | Cunningham et al. | 600/573 |
| 6,066,847 A | 5/2000 | Rosenthal | |
| 6,522,903 B1 | * 2/2003 | Berman et al. | 600/316 |

FOREIGN PATENT DOCUMENTS

| | | |
|---|---|---|
| WO | WO 00/49941 | 8/2000 |
| WO | WO 00/78210 A1 | 12/2000 |

OTHER PUBLICATIONS

Rickheim et al., *Type 2 Diabetes Basics*, International Diabetes Center, Institute for Research and Education, 2000, p. 16.

Jungheim and Koschinsky, *Risky Delay of Hypoglycemia Detection by Glucose Monitoring at the Arm*, Diabetes Care vol. 24, No. 7, pp. 1303–1304, Jul. 2001.

(List continued on next page.)

*Primary Examiner*—Eric F. Winakur
*Assistant Examiner*—Matthew Kremer
(74) *Attorney, Agent, or Firm*—Knobbe Martens Olson & Bear LLP

(57) ABSTRACT

A method calibrates a monitor that comprises a non-invasive blood constituent monitor and a traditional measurement system. The non-invasive blood constituent monitor includes a thermal gradient inducing element an analyzer window. A traditional monitor output representing a property of a blood constituent is generated by the traditional measurement system. A non-invasive monitor output representing the property of the whole blood constituent is generated by the non-invasive constituent monitor. The traditional monitor output and the non-invasive monitor output are compared to estimate an amount of error. The non-invasive monitor output is corrected by the amount of error.

26 Claims, 7 Drawing Sheets

OTHER PUBLICATIONS

McGarraugh, *Response to Jungheim and Koschinsky*, Diabetes Care vol. 24, No. 7, pp. 1304–1306, Jul. 2001.

U.S. Department of Health and Human Services, Food and Drug Administration, Center for Devices and Radiological Health, *Meeting of the Clinical Chemistry and Clinical Toxicology Devices Panel of the Medical Devices Advisory Committee*, Oct. 29, 2001.

McGarraugh et al., *Glucose Measurements Using Blood Extracted from the Forearm and the Finger*, TheraSense, Inc., 2001.

Ellison et al., *Rapid Changes in Postprandial Blood Glucose Produce Concentration Differences at Finger, Forearm, and Thigh Sampling Sites*, Diabetes Care vol. 25, No. 6, pp. 961–964, Jun. 2002.

* cited by examiner

CALIBRATOR CONFIGURED FOR USE WITH NONINVASIVE ANALYTE-CONCENTRATION MONITOR AND EMPLOYING TRADITIONAL MEASUREMENTS

RELATED APPLICATIONS

This application claims priority to U.S. Provisional Patent Application No. 60/313,082, filed Aug. 16, 2001, entitled ANALYTE MEASUREMENT ERROR CORRECTION METHOD AND DEVICE, the entire contents of which are hereby incorporated by reference.

BACKGROUND OF THE INVENTION

1. Field of the Invention

This invention relates generally to determining analyte concentrations within living tissue.

2. Description of the Related Art

Millions of diabetics are forced to draw blood on a daily basis to determine their blood glucose levels. A search for a non-invasive methodology to accurately determine blood glucose levels has been substantially expanded in order to alleviate the discomfort of these individuals.

SUMMARY OF THE INVENTION

A significant advance in the state of the art of non-invasive blood glucose analysis has been realized by an apparatus taught in U.S. Pat. No. 6,198,949, titled SOLID-STATE NON-INVASIVE INFRARED ABSORPTION SPECTROMETER FOR THE GENERATION AND CAPTURE OF THERMAL GRADIENT SPECTRA FROM LIVING TISSUE, issued Mar. 6, 2001; and by methodology taught in U.S. Pat. No. 6,161,028, titled METHOD FOR DETERMINING ANALYTE CONCENTRATION USING PERIODIC TEMPERATURE MODULATION AND PHASE DETECTION, issued Dec. 12, 2000; and in the Assignee's U.S. patent application Ser. No. 09/538,164, titled METHOD AND APPARATUS FOR DETERMINING ANALYTE CONCENTRATION USING PHASE AND MAGNITUDE DETECTION OF A RADIATION TRANSFER FUNCTION. Additional information relating to calibration of such non-invasive blood analysis is taught in U.S. Pat. No. 6,049,081, titled SUBSURFACE THERMAL GRADIENT SPECTROMETRY, issued Apr. 11, 2000; and by U.S. Pat. No. 6,196,046 B1, titled DEVICES AND METHODS FOR CALIBRATION OF A THERMAL GRADIENT SPECTROMETER, issued Mar. 6, 2001. The entire disclosure of all of the above mentioned patents and patent applications are hereby incorporated by reference herein and made a part of this specification.

U.S. Pat. No. 6,198,949 discloses a spectrometer for non-invasive measurement of thermal gradient spectra from living tissue. The spectrometer includes an infrared transmissive thermal mass, referred to as a thermal mass window, for inducing a transient temperature gradient in the tissue by means of conductive heat transfer with the tissue, and a cooling system in operative combination with the thermal mass for the cooling thereof. Also provided is an infrared sensor for detecting infrared emissions from the tissue as the transient temperature gradient progresses into the tissue, and for providing output signals proportional to the detected infrared emissions. A data capture system is provided for sampling the output signals received from the infrared sensor as the transient temperature gradient progresses into to the tissue. The transient thermal gradients arising due to the intermittent heating and cooling of the patient's skin generate thermal spectra which yield very good measurements of the patient's blood glucose levels.

Although the apparatus taught in the above-mentioned U.S. Pat. No. 6,198,949 has led to a significant advance in the state of the art of non-invasive blood glucose analysis, one possible source of error in such analysis arises due to physiological variation across the patient population. This variation, as well as other factors, can introduce systematic error into the measurements being performed.

In accordance with one embodiment, there is provided a method for calibrating a monitor comprising a non-invasive blood constituent monitor connected to a traditional measurement system via a data link. An amount of whole blood is withdrawn from a patient. A blood constituent in the amount of whole blood is analyzed with the traditional measurement system. A traditional monitor output representing a property of the blood constituent is generated. The thermal gradient inducing element of the non-invasive blood constituent monitor is placed in contact with a portion of the skin of the patient. The blood constituent in blood within the patient is analyzed by detecting thermal radiation at selected wavelengths. A non-invasive monitor output representing the property of the blood constituent is generated. The traditional monitor output and the non-invasive monitor output are compared to estimate an amount of error. The non-invasive monitor output is corrected based on the error.

In accordance with another embodiment, there is provided a blood constituent monitor that comprises a non-invasive blood constituent monitor that includes a thermal gradient inducing element. The non-invasive blood constituent monitor also includes an analyzer window. The blood constituent monitor also comprises a traditional measurement system that has a whole blood withdrawal portion and an analysis portion. The blood constituent monitor also comprises a data link that transfers data between the noninvasive blood constituent monitor and the traditional measurement system. The noninvasive blood constituent monitor and the traditional measurement system are permanently connected.

In accordance with another embodiment, there is provided a method for calibrating a non-invasive blood constituent monitor connected to a traditional measurement system via a data link. The operator determines whether there is a restricted period in effect. An on-site or an off-site measurement location is selected based on whether the restricted period is in effect. A traditional measurement of a blood constituent is performed at the selected measurement location using the traditional measurement system. A traditional monitor output representing a property of the blood constituent is generated. The analyzer window of the non-invasive blood constituent monitor is placed in contact with the skin of the patient. The blood constituent is analyzed with the non-invasive blood constituent monitor. A non-invasive monitor output representing the property of the blood constituent is generated. The traditional monitor output and the non-invasive monitor output are compared to estimate an error. The non-invasive monitor output is corrected based on the error.

In accordance with another embodiment, there is provided a blood constituent monitor that comprises a traditional measurement system configured to withdraw an amount of whole blood from a patient. The blood constituent monitor is also configured to analyze a blood constituent in the amount of whole blood to generate a traditional monitor output representing a property of the blood constituent. The blood constituent monitor also comprises a non-invasive monitor that has a thermal gradient inducing element configured to be placed in contact with the skin of the patient. The non-invasive monitor is configured to analyze the blood constituent in the patient to produce a non-invasive monitor output by detecting thermal radiation emitted by the blood constituent. The blood constituent monitor also comprises a data link connected to the traditional measurement system and connected to the non-invasive monitor. The data link is configured to transmit the output of the traditional measurement to the non-invasive monitor. The blood constituent monitor is configured to compare the traditional monitor output and the non-invasive monitor output.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

Having thus summarized the general nature of the invention, certain preferred embodiments and modifications thereof will become apparent to those skilled in the art from the detailed description herein having reference to the figures that follow, of which.

DETAILED DESCRIPTION OF THE PREFERRED EMBODIMENT

A method and device for reducing measurement error in a noninvasive monitor for measuring the concentration of an analyte, e.g., glucose, in the tissue of a patient is disclosed. The method involves measuring properties of the analyte in blood withdrawn from the patient. The method can also involve using the analyte property measurements to reduce patient-specific calibration error of the noninvasive monitor. In another variation, the noninvasive monitor, in combination with a whole blood adapter, measures analyte concentration in the patient's withdrawn blood, i.e., a makes a "whole blood" measurement. An apparatus for calibrating the noninvasive monitor measurement is also disclosed.

Monitor calibration error can arise from several sources, including physiological variation across the patient population. Patient-specific monitor calibration error can arise from, for example, the skin condition or the physical condition of the patient. This error can be estimated and corrected by performing a traditional, whole blood measurement of analyte concentration in each patient, comparing the result to a measurement by the non-invasive monitor, and correcting the monitor for any observed differences between the two measurements. In one embodiment, the traditional analyte concentration measurement is performed on blood withdrawn from the patient by using, for example, a needle, laser, lancet, finger-stick, or any other practical blood-withdrawal device. The traditional measurement selected is any of a number of highly accurate techniques well known to those skilled in the art. For example, an optical or colorimetric technique can be used. Other variations include using an amperometric technique, or a coulombometric technique.

Figure 1:
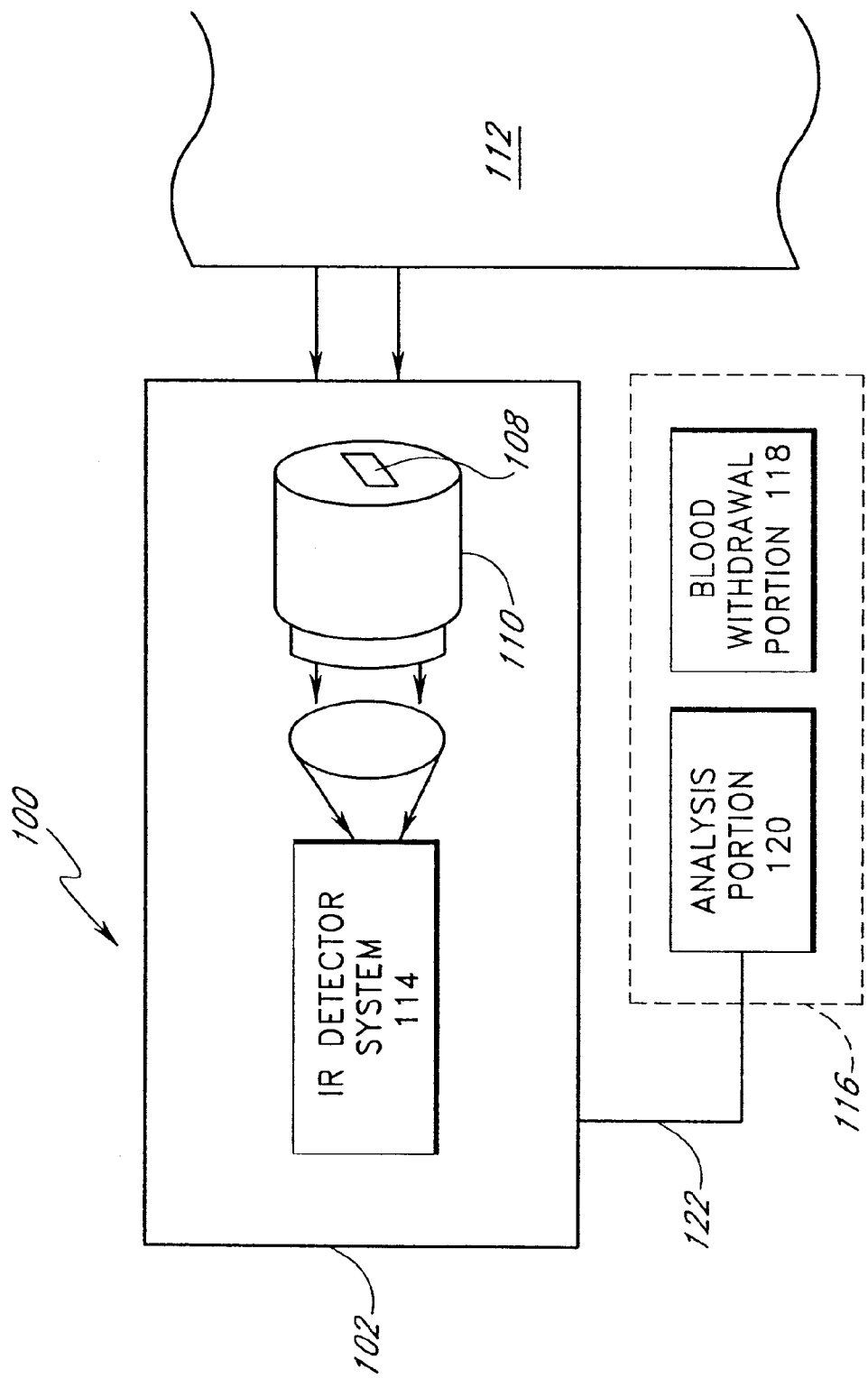
FIG. 1 shows a pictorial representation of a monitor that includes a non-invasive detection unit and a traditional measurement system.

As shown in FIG. 1, the monitor 100 comprises a non-invasive detection unit 102 and a traditional measurement system 116. In the illustrated embodiment, the noninvasive detection unit 102 comprises an analyzer window 108, a thermal element 110 capable of inducing a thermal gradient at the surface of the patient's skin 112, and an infrared radiation detector system 114 capable of measuring radiation emitted from the patient's skin or body at wavelengths selected to highlight or isolate the absorptive effects of the analyte of interest, for example, at one or more analyte absorbance wavelength peaks and at one or more reference wavelengths. However, one of skill in the art will appreciate that the noninvasive detection unit 102 can comprise any instrument which determines the concentration of an analyte of interest in a subject's tissue without withdrawal of blood from the subject.

In one embodiment, the traditional measurement system 116 has a blood-withdrawal portion 118 and an analysis portion 120. The traditional measurement system 116, via the analysis portion 120, is capable of analyzing blood withdrawn from the patient with the withdrawal portion 118 and providing a value or data to the monitor indicating analyte concentration in the blood withdrawn. Generally, the blood-withdrawal portion 118 comprises a needle, laser, lancet, finger-stick, etc., as well as any supporting hardware used for holding a withdrawn blood sample and/or placing the sample on or in the analysis portion 120.

In one embodiment, shown in FIG. 1, the analysis portion 120 is a separate unit connected to the noninvasive detection unit 102 through a data communication line 122 to facilitate communication of analyte-concentration information to the noninvasive detection unit 102. The analysis portion 120 can also be made as an integral component of the monitor 100. In one preferred variation of the monitor 100, the analysis portion 120 of the traditional measurement system 116 is an electro-chemical monitor. In this embodiment, the monitor 100 is configured to receive a conventional whole blood electrochemical test strip with blood added thereto. The analysis portion 120 of the traditional measurement system 116 can then perform the electrochemical analyte measurement.

Both the integral construction of the monitor 100 and the use of the data link 122 advantageously eliminate human transcription, which would otherwise be a source of human transcription error. Human transcription involves the manual entry, using an input device, such as a dial, keyboard, or other similar manual input device, of a value into a measurement device, such as the monitor 100. The transcription error avoided by the construction of the monitor 100 would occur if the user entered a wrong value using the input device. Such errors, which would cause all subsequent measurements to be inaccurate, would otherwise be very difficult to eliminate.

Advantageously, at least the blood withdrawal portion 118 of the device 116 may be configured as a single use item. In one embodiment, the blood withdrawal portion 118 of the device 116 is a single use device, i.e., one configured to be used only once.

Figure 2:
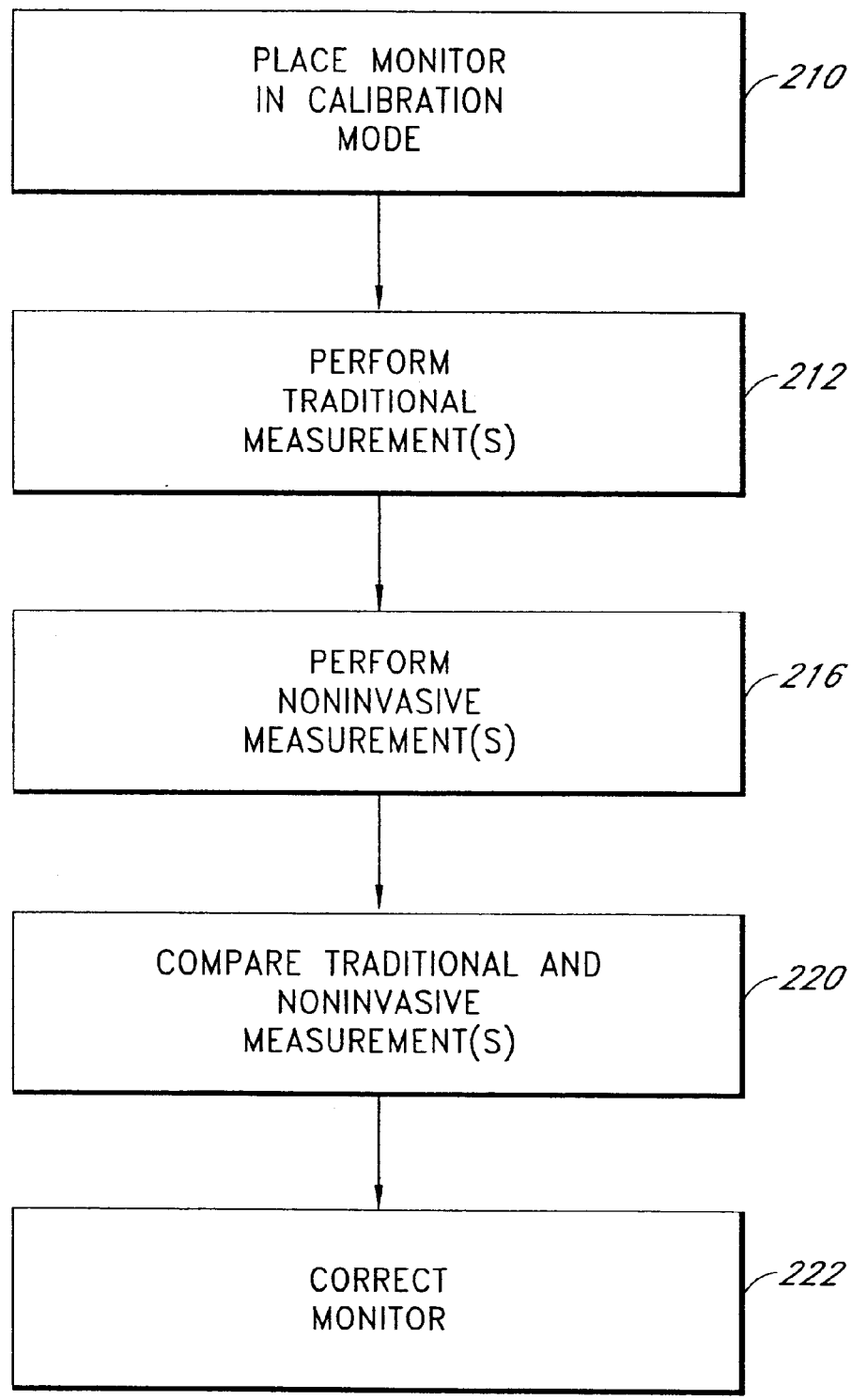
FIG. 2 shows a process flow for calibrating the monitor of FIG. 1.

FIG. 2 is a flow chart of a method of operation of the monitor 100. In one embodiment of this method, the unit 102 comprises a thermal element 110 capable of inducing a thermal gradient at the surface of the patient's skin 112, as described above. The method may comprise switching the monitor 100 to a patient calibration mode in a step 210. Then in a step 212, the operator performs a traditional measurement using the analysis device 116. This is done by withdrawing a blood sample from the patient and analyzing the blood sample in the device 116 to determine the analyte concentration of the blood sample. In another embodiment, the step 212 comprises performing multiple measurements to produce a series of data. These data can be manipulated to yield numerical values relating to the analyte concentration of the blood.

In a step 216, the operator uses the noninvasive detection unit 102 to measure the analyte concentration of the blood. In one embodiment of the method shown in FIG. 2, the step 216 comprises placing the thermal gradient inducing means of the monitor 100 in contact with the patient's skin 112 at a measurement site, inducing a thermal gradient in the patient's skin, and performing an analyte measurement by detecting and analyzing thermal radiation at selected wavelengths. As in the step 212, another embodiment of the step 216 comprises performing multiple measurements to produce a series of data representing the analyte concentration of the blood. As mentioned above, one of skill in the art will appreciate that the noninvasive detection unit 102 can comprise any instrument which determines the concentration of an analyte of interest in a subject's tissue without withdrawal of blood from the subject.

Next in a step 220, the analyte measurements performed in the step 212 and the step 216 are compared to estimate the calibration error. Finally, in a step 222 the measurement output of the monitor is corrected using the calibration error estimated in step 220 to correct for the patient-specific monitor calibration error.

Figure 2A:
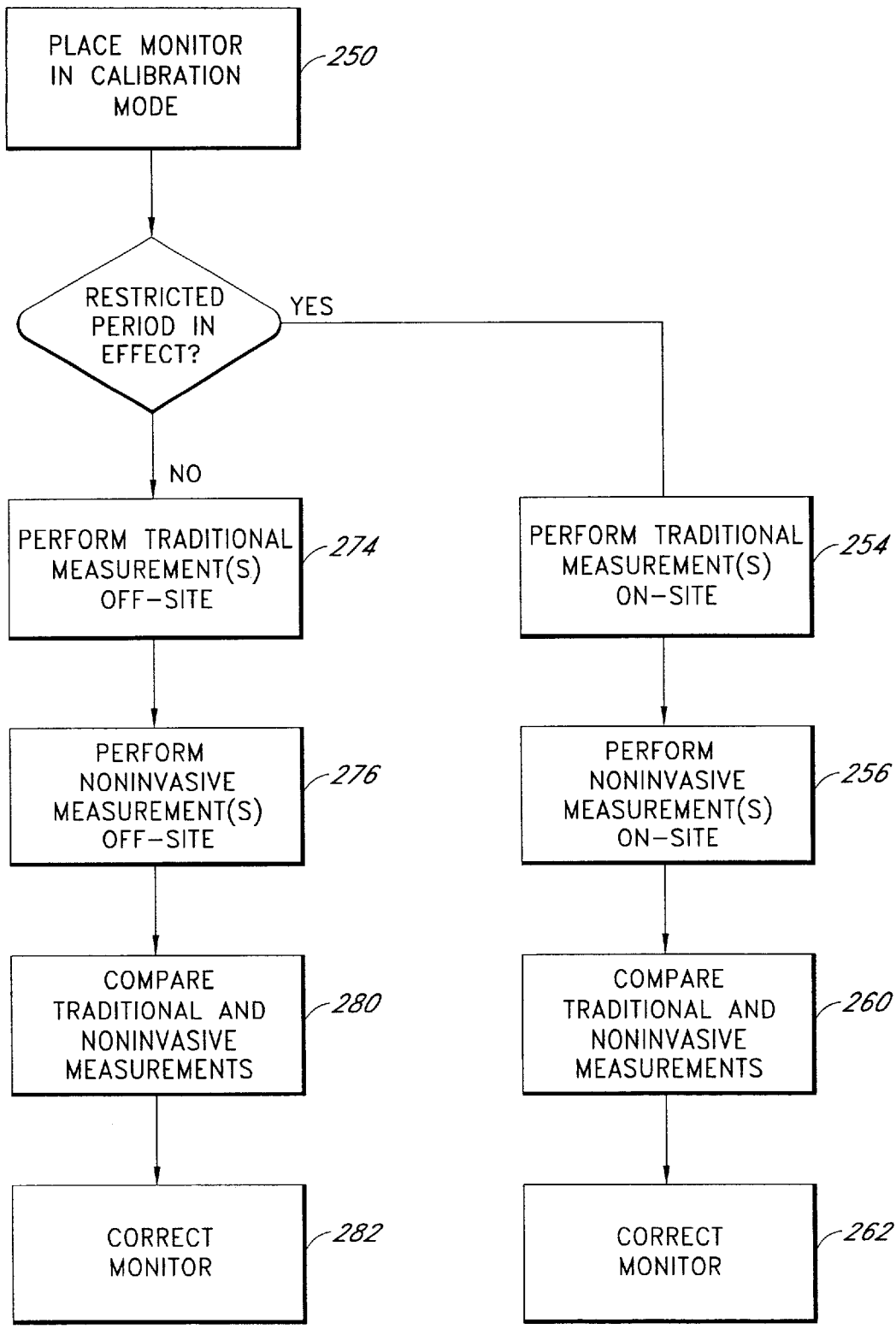
FIG. 2A shows a variation of the process flow of FIG. 2 wherein a restricted period may be applied after the subject eats.

FIG. 2A is a flow chart of another variation of the method of operation of the monitor 100. This variation addresses where and when measurements are to be taken. More particularly, the method involves the choice of a location on a subject's body at which to take the analyte measurement, preferably based on the amount of time that has elapsed since the last time the subject ate. A restricted period commences after the subject eats. This restricted period is characterized by a restriction on where the subject may take analyte measurements; specifically, the subject is restricted to taking measurements "on-site" (on a finger or fingertip, or alternatively, anywhere distal of the wrist) during a restricted period.

In contrast, when no restricted period is in effect (i.e., the designated time interval has elapsed since the last time the subject ate) the subject may take analyte measurements either on-site or at an off-site measurement location such as, for example, the forearm. It is to be understood, however, that an "off-site" measurement location refers to any location other than the on-site locations.

The method shown in FIG. 2A may comprise switching the monitor 100 to a patient calibration mode in a step 250. Then in a step 252, the operator determines whether there is a restricted period in effect. In one embodiment, the restricted period lasts from about 0.5 to about 3 hours after the subject eats. In another embodiment, the restricted period lasts from about 1.0 to about 2 hours. In another embodiment, the restricted period lasts from about 1.5 to about 2 hours. In a presently preferred embodiment, the restricted period lasts about 2 hours. If there is a restricted period in effect, then in a step 254, the operator performs a traditional measurement "on-site" using the analysis device 116. This is done by withdrawing a blood sample from the patient and analyzing the blood sample in the device 116 to determine the analyte concentration of the blood sample.

Then in a step 256, the noninvasive detection unit 102 measures the analyte concentration of the blood on-site. The step 256 may comprise placing the thermal gradient inducing means of the monitor 100 in contact with the patient's skin 112 at a measurement site, inducing a thermal gradient in the patient's skin, and performing an analyte measurement by detecting and analyzing thermal radiation at selected wavelengths. As mentioned above, however, one of skill in the art will appreciate that the noninvasive detection unit 102 can comprise any instrument which determines the concentration of an analyte of interest in a subject's tissue without withdrawal of blood from the subject.

Next in a step 260, the analyte measurements performed in the step 254 and the step 256 are compared to estimate the calibration error. Finally, in a step 262 the measurement output of the monitor is corrected using the calibration error estimated in step 260 to correct for the patient-specific monitor calibration error.

If no restricted period in effect, then in a step 274, the operator performs a traditional measurement at an off-site measurement location using the analysis device 116. As mentioned above, the traditional measurement at the off-site measurement location is done by withdrawing a blood sample from the patient and analyzing the blood sample in the device 116 to determine the analyte concentration of the blood sample.

In a step 276, the noninvasive detection unit 102 measures, at an off-site measurement location, the analyte concentration of the blood. As above, the step 276 may comprise placing the thermal gradient inducing means of the monitor 100 in contact with the patient's skin 112 at a measurement site, inducing a thermal gradient in the patient's skin, and performing an analyte measurement by detecting and analyzing thermal radiation at selected wavelengths. Again, the noninvasive detection unit 102 can comprise any instrument which determines the concentration of an analyte of interest in a subject's tissue without withdrawal of blood from the subject.

Next in a step 280, the analyte measurements performed in the step 274 and the step 276 are compared to estimate the calibration error. Finally, in a step 282 the measurement output of the monitor is corrected using the calibration error estimated in step 280 to correct for the observed patient-specific monitor calibration error.

In any of the methods described herein, calibration can also be performed by using the noninvasive monitor to analyze analyte concentration in withdrawn blood. In this embodiment, the analysis portion 120 of the analysis device 116 would be omitted. Instead, the monitor 100 performs the analyte concentration measurement on a blood sample withdrawn from the patient. This is called whole blood analysis.

Figure 3A:
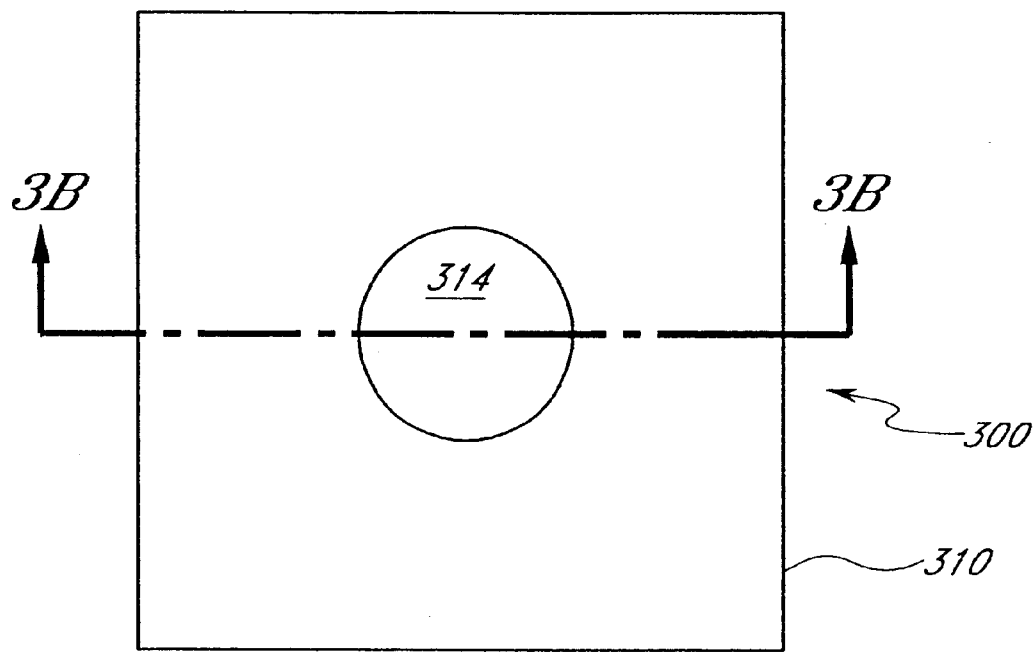
FIG. 3A shows a top view of a whole blood adapter.
Figure 3B:
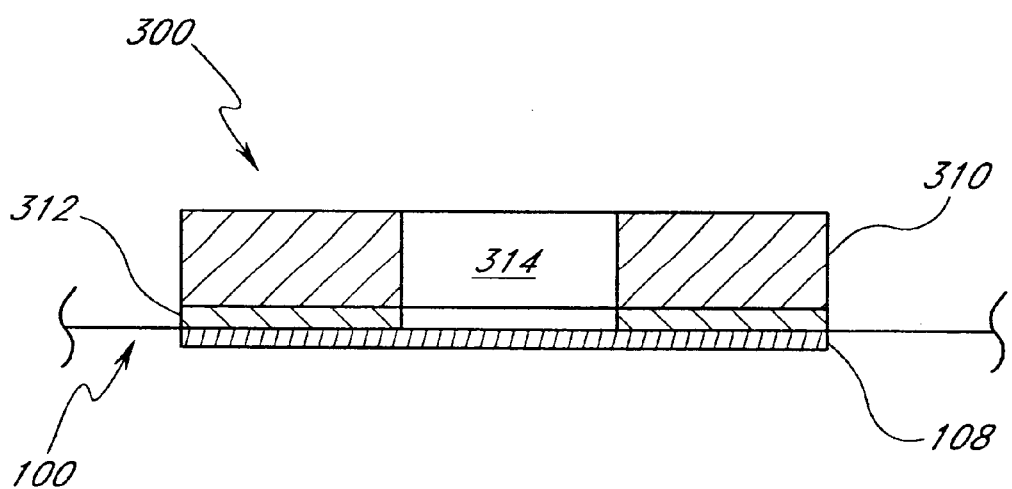
FIG. 3B shows a cross-sectional view of the whole blood adapter of FIG. 3A.

FIGS. 3A and 3B depict a whole blood adapter 300 which can be used to facilitate whole blood analysis by any noninvasive monitor having a window, lens, or other opening for passing or receiving energy to or from a sample or living tissue. In one embodiment the adapter 300 comprises a base material 310. The material 310 is preferably a hydrophobic material, e.g., Kapton. The adapter 300 is configured to be applied to the analyzer window 108 of the monitor 100 and sized to cover a large portion of the window 108. The adapter 300 also has a whole blood accommodating volume 314 configured to receive a small amount of blood that extends between openings positioned on opposite sides of the base material 310.

In another embodiment, the adapter 300 also comprises an adhesive backing 312. The adhesive backing 312 is selected from materials that do not give any analyte absorption signature, i.e., those materials that do not emit thermal radiation in the same spectra as the analyte. This has the effect of "passivating" the portions of the window covered by the adhesive 312.

In operation, the adapter 300 is applied to the analyzer window 108. Then a drop of blood is placed in the whole blood accommodating volume 314. Once the blood is applied to the whole blood accommodating volume 314, the analyte concentration of the blood is measured in the usual manner. After the monitor 100 performs the measurement, the adapter 300 is removed from the window 108 of the monitor 100, and any blood left on the window is removed. This can be done using a sterilizing solution, such as isopropyl alcohol or other well known sterilizing solutions.

Figure 4A:
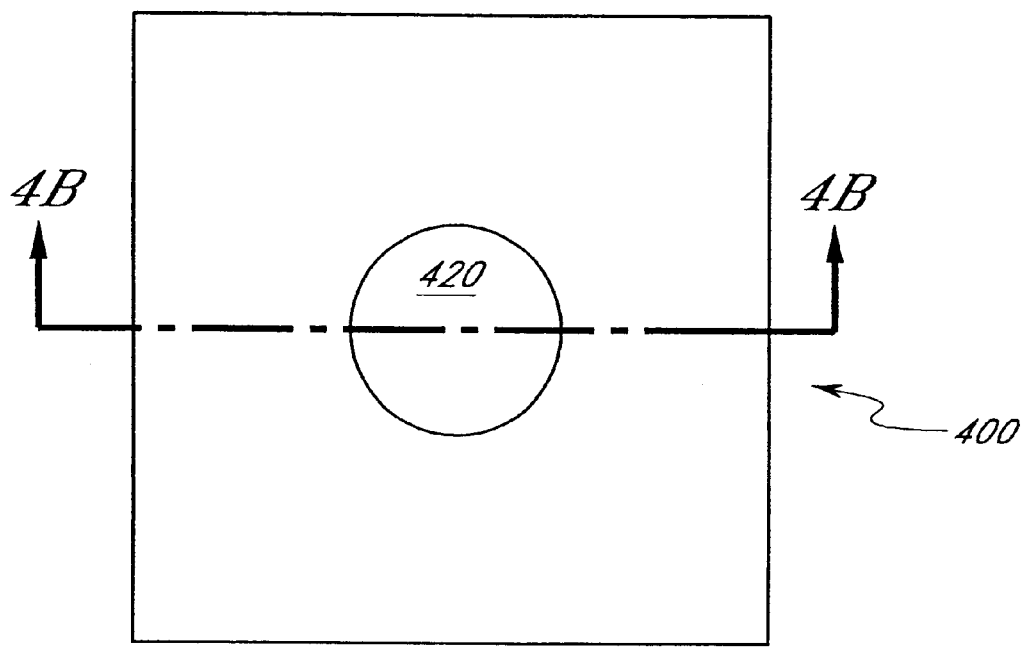
FIG. 4A shows a top view of a variation of the whole blood adapter.
Figure 4B:
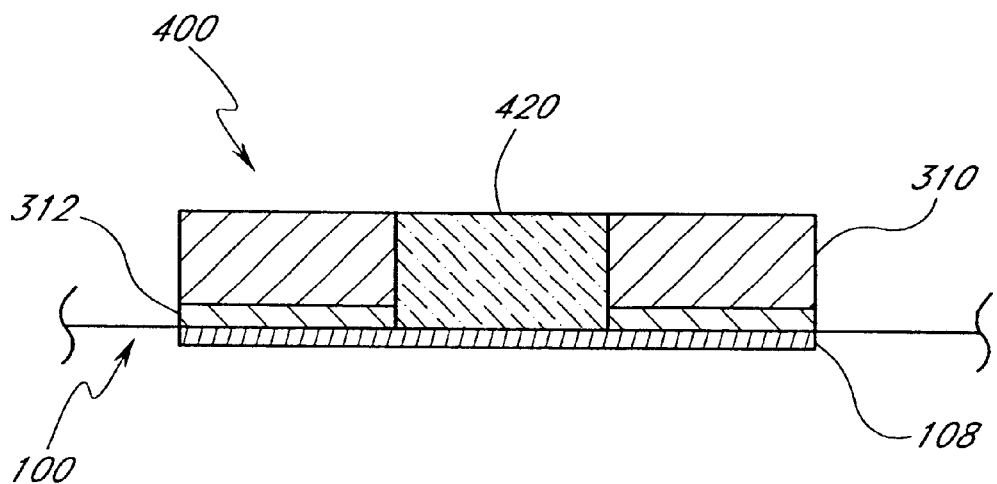
FIG. 4B shows a cross-sectional view of the whole blood adapter of FIG. 4A.

In one variation shown in FIGS. 4A and 4B, an adapter 400 similar to the adapter 300 has a wicking medium 420 that captures the blood using capillary forces. Capillary forces cause the blood to be drawn into the wicking medium. In operation, after the adapter 400 is removed from the window 108 of the monitor 100, the blood remains captured in the wicking material 420. This reduces the amount of blood remaining on the window 108 after the adapter 400 is removed. Thus, a simple wipe with an alcohol soaked pad is sufficient to clean the window.

Figure 5A:
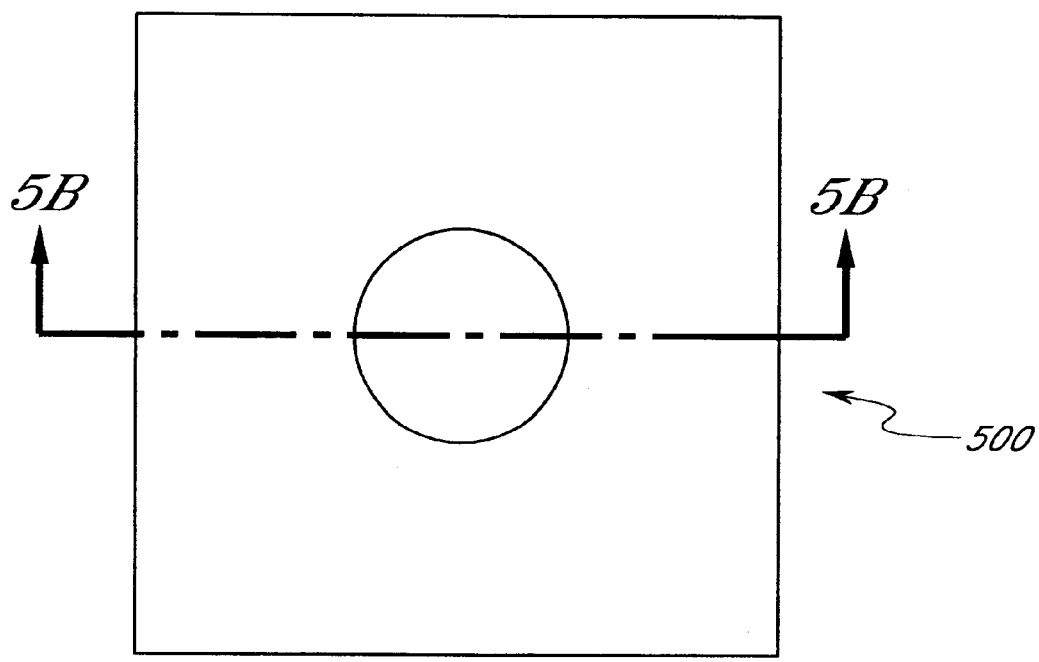
FIG. 5A shows a top view of another variation of the whole blood adapter.
Figure 5B:
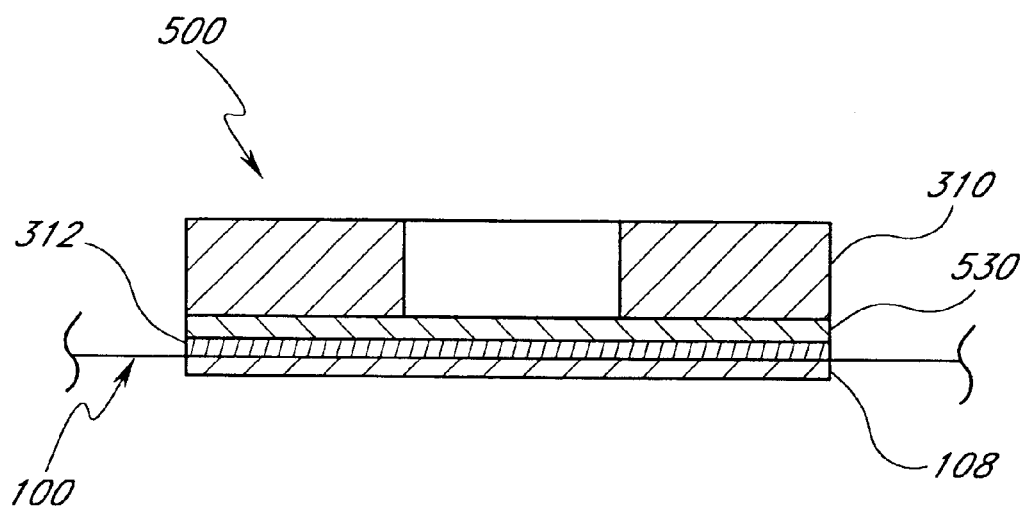
FIG. 5B shows a cross-sectional view of the whole blood adapter of FIG. 5A.

In another embodiment shown in FIGS. 5A and 5B, an adapter 500 comprises a thin optically transparent material layer 530 to prevent the blood from coming into contact with the analyzer window 108. Suitable materials for the layer 530 include mylar, vinyl, and polypropylene. After the measurement is made the adapter 500, including the thin layer 530, is removed and discarded. There is no need to clean the window 108 as blood did not contact the window. In the embodiments illustrated in FIGS. 3A–5B, a column of blood is captured in the whole blood accommodating volume having an outer diameter approximately equal to the diameter of the opening in the base material and a height approximately equal to the thickness of the base material. The amount of the blood sample required is limited by the diameter of the opening in the base material.

Figure 6A:
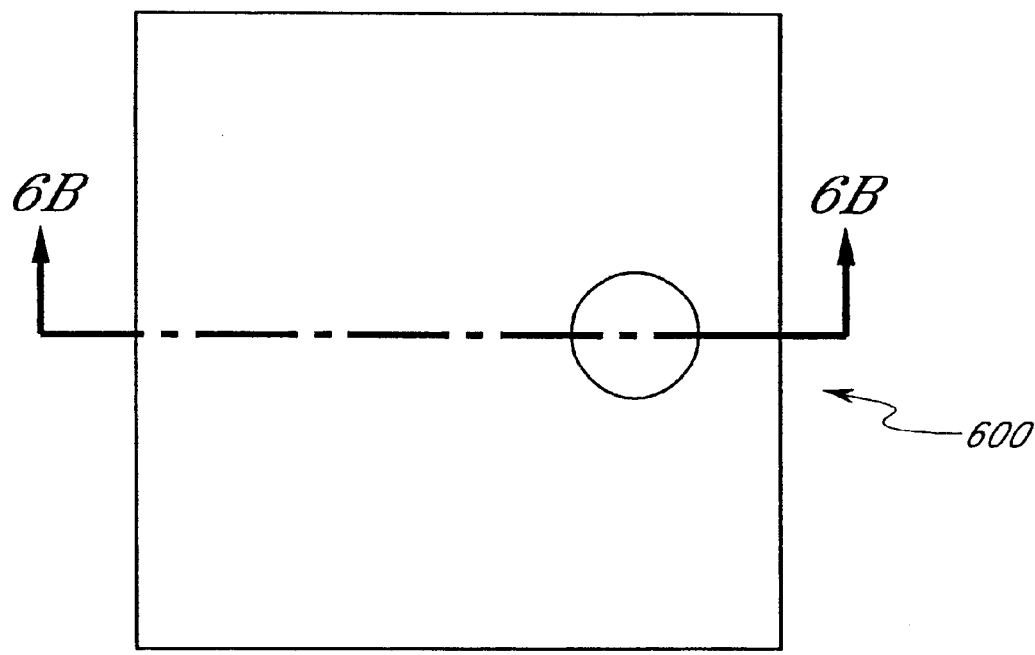
FIG. 6A shows a top view of another variation of the whole blood adapter.
Figure 6B:
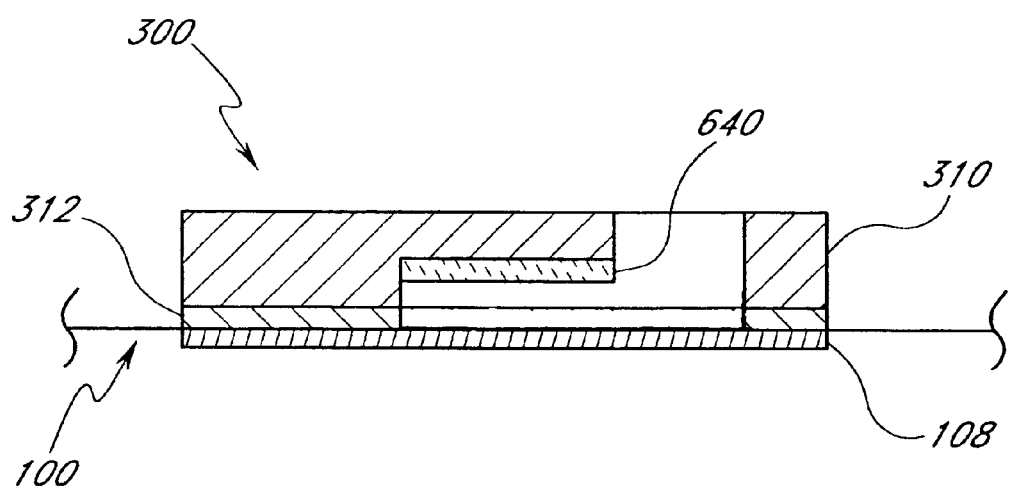
FIG. 6B shows a cross-sectional view of the whole blood adapter of FIG. 6A.

In yet another embodiment shown in FIG. 6, an adapter 600 is configured to further limit the amount of the blood sample by further reducing the height of the blood column and by reducing the diameter of the opening in the base material. As a result, the whole blood accommodating volume is reduced. Under normal operating conditions the noninvasive analyzer disclosed in U.S. Pat. No. 6,198,949 will sense an analyte to a depth of several hundred microns in the whole blood or noninvasive sample. If the height of the whole blood sample is reduced, the measurement will be made on only the available height. Such a measurement can be performed by incorporating a neutral absorption material 640 such as polyethylene, or silicon into the adapter 600. The material 640 is positioned in the adapter 600 so that when the blood is within the adapter 600 and when the adapter is positioned on the window 108, the blood is between the material 640 and the window 108. The material 640 must not absorb infrared energy in the wavelength ranges absorbed by the analyte, the blood, or the normal body tissues.

Whole blood analysis can also be performed under the measurement location protocol described above. As discussed above, the whole blood adapters will be used in conjunction with blood withdrawn either from the on-site location or from the off-site location. The blood withdrawal location will preferably be based on the amount of time that has elapsed since the last time the subject ate. As discussed above, during the restricted period, which commences after the subject eats, the subject is restricted to withdrawing blood "on-site." In contrast, when no restricted period is in effect (i.e., the designated time interval has elapsed since the last time the subject ate) the subject may withdraw blood either on-site or at an off-site location such as, for example, the forearm. As above, it is to be understood, however, that the "off-site" location refers to any location other than the on-site locations.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

What is claimed is:

1. A method for calibrating a non-invasive blood constituent monitor connected to a traditional measurement system via a data link, the non-invasive monitor having an analyzer window, the method comprising:

determining whether there is a restricted period in effect;

selecting a first measurement location distal of a wrist or a second measurement location other than distal of the wrist based on whether a restricted period is in effect;

performing a traditional measurement of a blood constituent at the selected measurement location using the traditional measurement system;

generating a traditional monitor output representing a property of the blood constituent;

placing the analyzer window of the non-invasive blood constituent monitor in contact with the skin of a patient;

analyzing the blood constituent in blood within the patient with the non-invasive blood constituent monitor;

generating a non-invasive monitor output representing the property of the blood constituent;

comparing the traditional monitor output and the non-invasive monitor output to estimate an error; and correcting the non-invasive monitor output based on said error.

2. The method of claim 1, wherein placing the analyzer window of the non-invasive blood constituent monitor in contact with the skin of the patient comprises placing the analyzer window in contact with the skin of the patient at said first measurement location or said second measurement location based on whether a restricted period is in effect.

3. The method of claim 1, wherein placing an analyzer window of the non-invasive blood constituent monitor in contact with the skin of the patient further comprises placing a thermal gradient inducing element of said non-invasive blood constituent monitor in contact with the skin of the patient.

4. The method of claim 1, further comprising correcting subsequent non-invasive monitor outputs based on said error.

5. The method of claim 1, wherein performing a traditional measurement comprises:
   withdrawing an amount of whole blood from the patient, and
   analyzing the blood constituent in the amount of whole blood with the traditional measurement system.

6. The method of claim 1 wherein generating a traditional monitor output representing a property of the blood constituent comprises generating a traditional monitor output representing the concentration of blood glucose.

7. The method of claim 1 wherein performing a traditional comprises performing an electro-chemical analysis of the whole blood withdrawn.

8. The method of claim 1 wherein determining whether there is a restricted period in effect comprises measuring an amount of time since the patient has eaten.

9. The method of claim 8 wherein the amount of time measured is from about 0.5 hour to about 3 hours.

10. The method of claim 8, wherein the amount of time measured s from about 1 hours to about 2 hours.

11. The method of claim 8, wherein the amount of time measured is from about 1.5 hours to about 2 hours.

12. The method of claim 8, wherein the amount of time measured is about 2 hours.

13. A method for calibrating a non-invasive blood constituent monitor, the method comprising:
   selecting a first measurement location distal of a wrist or second measurement location other than distal of the wrist;
   performing an invasive measurement of a blood constituent at the selected measurement location using an invasive blood constituent monitor;
   generating an invasive monitor output representing a property of the blood constituent;
   performing a non-invasive measurement of the blood constituent at the selected measurement location using the non-invasive blood constituent monitor;
   generating a non-invasive monitor output representing the property of the blood constituent;
   comparing the invasive monitor output and the non-invasive monitor output to estimate an error;
   correcting the non-invasive monitor output based on said error; and
   determining whether there is a restricted period in effect;
   wherein selecting a first measurement location distal of the wrist or a second measurement location other than distal of the wrist comprises selecting the first or second measurement location based on whether there is a restricted period in effect.

14. The method of claim 13, further comprising correcting subsequent non-invasive monitor outputs based on said error.

15. The method of claim 13, wherein determining whether there is a restricted period in effect comprises measuring an amount of time since a subject has eaten.

16. The method of claim 15, wherein the amount of time measured is from about 0.5 hour to about 3 hours.

17. The method of claim 15, wherein the amount of time measured is from about 1 hours to about 2 hours.

18. The method of claim 15, wherein the amount of time measured is from about 1.5 hours to about 2 hours.

19. The method of claim 15, wherein the amount of time measured is about 2 hours.

20. A method foil calibrating a non-invasive blood constituent monitor, the method comprising:
   selecting, based on patient-specific parameters, a first measurement location distal of a wrist or a second measurement location other than distal of the wrist;
   performing an invasive measurement of a blood constituent at the selected measurement location using an invasive blood constituent monitor;
   generating an invasive monitor output representing a property of the blood constituent;
   performing a non-invasive measurement of the blood constituent at the selected measurement location using the non-invasive blood constituent monitor;
   generating a non-invasive monitor output representing the property of the blood constituent;
   comparing the invasive monitor output and the non-invasive monitor output to estimate an error; and
   correcting the non-invasive monitor output based on said error;
   wherein selecting based on patient-specific parameters comprising determining whether there is a restricted period in effect.

21. The method of claim 20, further comprising correcting subsequent non-invasive monitor outputs based on said error.

22. The method of claim 20, wherein determining whether there is a restricted period in effect comprises measuring an amount of time since a subject has eaten.

23. The method of claim 22 wherein the amount of time measured is from about 0.5 hour to about 3 hours.

24. The method of claim 22, wherein the amount of time measured is from about 1 hours to about 2 hours.

25. The method of claim 22 wherein the amount of time measured is from about 1.5 hours to about 2 hours.

26. The method of claim 22, wherein the amount of time measured is about 2 hours.

* * * * *

UNITED STATES PATENT AND TRADEMARK OFFICE
CERTIFICATE OF CORRECTION

PATENT NO. : 6,678,542 B2
DATED : January 13, 2004
INVENTOR(S) : Braig et al.

It is certified that error appears in the above-identified patent and that said Letters Patent is hereby corrected as shown below:

Column 10,
Line 18, please replace "foil" with -- for --.

Signed and Sealed this

First Day of February, 2005

JON W. DUDAS
*Director of the United States Patent and Trademark Office*